(12) United States Patent
Askenazi

(10) Patent No.: US 6,594,587 B2
(45) Date of Patent: Jul. 15, 2003

(54) METHOD FOR ANALYZING BIOLOGICAL ELEMENTS

(75) Inventor: Manor Askenazi, Cambridge, MA (US)

(73) Assignee: Monsanto Technology LLC, St. Louis, MO (US)

( * ) Notice: Subject to any disclaimer, the term of this patent is extended or adjusted under 35 U.S.C. 154(b) by 139 days.

(21) Appl. No.: 09/739,794

(22) Filed: Dec. 20, 2000

(65) Prior Publication Data

US 2002/0123847 A1 Sep. 5, 2002

(51) Int. Cl.$^7$ ............................ G06F 19/00; C12Q 1/68
(52) U.S. Cl. ............................................. 702/19; 435/6
(58) Field of Search ................................ 702/19; 435/6

(56) References Cited

U.S. PATENT DOCUMENTS 6,144,962 A  11/2000  Weinberg et al.

OTHER PUBLICATIONS

Schwikowski et al., "The Deferred Path Heuristic for the Generalized Tree Alignment Problem", J. of Computational Biology Bol. 4 No. 3 (1997) pp. 415–431.*

Choukhmane, "Heuristic for the Steiner Tree Problem", R.A.I.R.O. Recherche opérationnelle/Operations Research, 12(2):207–212 (1978).

Eisenberg, et al., "Protein Function in the Post–Genomic Era," Nature, vol. 405, No. 6788, pp. 823–836 (2000).

Fellenberg and Mewes, "Interpreting Clusters of Gene Expression Profiles in Terms of Metabolic Pathways", http://www.bioinfo.de/isb/gcb99/poster/fellenberg/, (printed on Nov. 13, 2000).

"From Sequence to Function—An Introduction to the KEGG Project", http://www.genome.ad.jp/kegg/docs/intro.html, (printed on Oct. 25, 2000).

Rayward–Smith and Clare, "On Finding Steiner Vertices", Networks 16, 283–294 (1986).

Takahashi and Matsuyama, An Approximate Solution for the Steiner Problem in Graphs, Math. Jap. 24, 573–577(1980).

Uetz, et al., A Comprehensive Analysis of Protein–Protein Interactions in Saccharomyces cerevisiae, Nature, vol. 403, No. 6770, pp. 623–627 (2000).

* cited by examiner

Primary Examiner—John S. Brusca
(74) Attorney, Agent, or Firm—Lawrence M. Lavin, Jr.; Thomas E. Kelley; Arnold & Porter

(57) ABSTRACT

The present invention is in the field of bioinformatics, particularly as it pertains to determining the associations of biological elements. More specifically, the present invention relates to the determination of associations among a set of biological elements using an algorithm that is capable of generating a Steiner tree.

34 Claims, 8 Drawing Sheets

METHOD FOR ANALYZING BIOLOGICAL ELEMENTS

FIELD OF THE INVENTION

The present invention is in the field of bioinformatics, particularly as it pertains to determining the associations of biological elements. More specifically, the present invention relates to the determination of associations among a set of biological elements using an algorithm that is capable of generating a Steiner tree.

BACKGROUND OF THE INVENTION

Recent advances across the spectrum of the biological sciences have allowed researchers to compile large amounts of biological data from a myriad of organisms. For example, advances in techniques for sequencing long stretches of genomic deoxyribonucleic acid (DNA) have allowed investigators to collect vast nucleic acid sequence data rapidly. Similarly, advances in RNA transcript profiling have facilitated the rapid acquisition of large amounts of data on the relative rates of transcription of genes in varying conditions.

The relationships among the discrete elements within the data collected, however, are often difficult to ascertain. For example, an RNA transcript profiling assay will often produce results that indicate that a set of genes is transcribed at a relatively high rate under a certain environmental condition. After acquisition of the data, however, the operative associations that resulted in the higher rate of transcription of the set of genes are often poorly understood.

The difficulty of determining the associations among biological elements is not limited to genes, however. For example, correlations among seemingly unrelated enzymes, enzymatic pathways, non-enzyme proteins, substrates, or other biological characteristics are often easier to demonstrate than to explain.

One conventional method for determining associations among a group of biological characteristics involves the use of graphs that show relationships among those biological characteristics (biological elements). These graphs are networks comprising vertices and edges. The vertices, which can be represented by discrete shapes such as circles, represent the biological elements. A relationship between any two of the biological elements is shown by connecting the two vertices that represent the two biological elements with edges, which can be represented as a line segment that connects the two vertices. A single vertex can be connected to multiple other vertices with multiple edges. Multiple vertices connected by multiple edges form a network.

FIG. 1 shows an illustrative graph of a simple network of vertices and edges generally at 10. A first vertex 12 is shown connected to a second vertex 14 with an edge 16. The vertices of the network 10 are labeled with the letters A through P for illustrative purposes.

Graphs such as the one shown in FIG. 1 have been described. Examples of graphs of enzymatic and genetic networks can be found in the Kyoto Encyclopedia of Genes and Genomes (http://www.genome.ad.jp/kegg/). The KEGG graph represents enzymatic relationships among various proteins. Graphs such as those provided by KEGG can be used by researchers, for example, who have information that indicates that two or more enzymes are related somehow, but who are unsure in which enzymatic pathways the enzymes function and how those pathways connect. By examining the KEGG graphs associated with the enzymes, researchers can examine multiple known pathways for potential relationships.

Although KEGG graphs (see, for example, Eisenberg et al., Protein Function in the Post-Genomic Era, Nature, Volume 405, Number 6788, Pages 823–826 (2000), Uetz et al., A Comprehensive Analysis of Protein—Protein Interactions in *Saccharomyces cerevisiae,* Nature, Volume 403, Number 6770, Page 623–627 (2000), each of which is herein incorporated by reference in its entirety) are useful for viewing associations, they are limited in their applicability. A researcher likely will examine significant amounts of information in an attempt to determine the associations that exist. Although KEGG graphs allow a researcher to examine the entire set of graphs known to contain the enzymes of interest for associations, they do not filter out certain unwanted and unrelated information.

One proposed solution to the problem of reducing the irrelevant or less relevant information in graphs with multiple enzymatic pathways is to input one or more enzymes and extract any valid pathways in which the enzymes of interest occur (Fellenberg and Mewes, Interpreting Clusters of Gene Expression Profiles in Terms of Metabolic Pathways, MIPS, Max-Planck-Institut f. Biochemie, http://www.bioinfo.de/isb/gcb99/poster/fellenberg/). This approach, however, is restricted to valid metabolic pathways, i.e. pathways with no unaccounted for intermediates.

What is needed in the art are refined methods for determining the associations among specified biological elements within a larger set of elements with known biorelationships.

SUMMARY OF THE INVENTION

The present invention is in the field of bioinformatics, particularly as it pertains to determining the associations of biological elements. More specifically, the present invention relates to the determination of associations among a set of biological elements using an algorithm that is capable of generating a Steiner tree.

The present invention includes and provides a method for analyzing biological elements, comprising: a) providing a first set of biological elements; b) providing a graph representing relationships among a second set of biological elements, wherein the biological elements of the second set of biological elements are represented as vertices of the graph and biorelationships between the biological elements of the second set of biological elements are represented as edges of the graph, and wherein the second set of biological elements comprises the first set of biological elements; and, c) applying an algorithm capable of generating a Steiner Tree to the first set of biological elements and the graph to create a Steiner subgraph, wherein the Steiner subgraph comprises vertices from the graph corresponding to the first set of biological elements and further comprises edges and vertices from the graph connecting the vertices from the graph corresponding to the first set of biological elements.

The present invention includes and provides a method for analyzing genes, comprising: a) providing a first set of genes; b) providing a graph representing relationships among a second set of genes, wherein the genes of the second set of genes are represented as vertices of the graph and biorelationships between the genes of the second set of genes are represented as edges of the graph, and wherein the second set of genes comprises the first set of genes; and, c) applying an algorithm capable of generating a Steiner Tree to the first set of genes and the graph to create a Steiner subgraph, wherein the Steiner subgraph comprises vertices from the graph corresponding to the first set of genes and further comprises edges and vertices from the graph connecting the vertices from the graph corresponding to the first set of genes.

The present invention includes and provides a program storage device readable by a machine, tangibly embodying a program of instructions executable by a machine to perform method steps to analyze biological elements, the method steps comprising: a) providing a first set of biological elements; b) providing a graph representing relationships among a second set of biological elements, wherein the biological elements of the second set of biological elements are represented as vertices of the graph and biorelationships between the biological elements of the second set of biological elements are represented as edges of the graph, and wherein the second set of biological elements comprises the first set of biological elements; and, c) applying an algorithm capable of generating a Steiner Tree to the first set of biological elements and the graph to create a Steiner subgraph, wherein the Steiner subgraph comprises vertices from the graph corresponding to the first set of biological elements and further comprises edges and vertices from the graph connecting the vertices from the graph corresponding to the first set of biological elements.

The present invention includes and provides a program storage device readable by a machine, tangibly embodying a program of instructions executable by a machine to perform method steps to analyze genes, the method steps comprising: a) providing a first set of genes; b) providing a graph representing relationships among a second set of genes, wherein the genes of the second set of genes are represented as vertices of the graph and biorelationships between the genes of the second set of genes are represented as edges of the graph, and wherein the second set of genes comprises the first set of genes; and, c) applying an algorithm capable of generating a Steiner Tree to the first set of genes and the graph to create a Steiner subgraph, wherein the Steiner subgraph comprises vertices from the graph corresponding to the first set of genes and further comprises edges and vertices from the graph connecting the vertices from the graph corresponding to the first set of genes.

The present invention includes and provides a method for analyzing biological elements, comprising: a) providing a first set of biological elements; b) providing a graph representing relationships among a second set of biological elements, wherein the biological elements of the second set of biological elements are represented as vertices of the graph and biorelationships between the biological elements of the second set of biological elements are represented as edges of the graph, and wherein the second set of biological elements comprises the first set of biological elements; and, c) applying an algorithm capable of generating a Steiner Tree to the first set of biological elements and the graph to create a Steiner subgraph.

DETAILED DESCRIPTION OF THE INVENTION

Described herein are methods for determining the associations among a set of biological elements using an algorithm capable of generating a Steiner Tree. Also described herein are program storage devices readable by a machine, tangibly embodying a program of instructions executable by a machine to perform method steps to analyze biological elements. The present invention allows for the rapid determination of potential associations among biological elements within a set.

Figure 2:
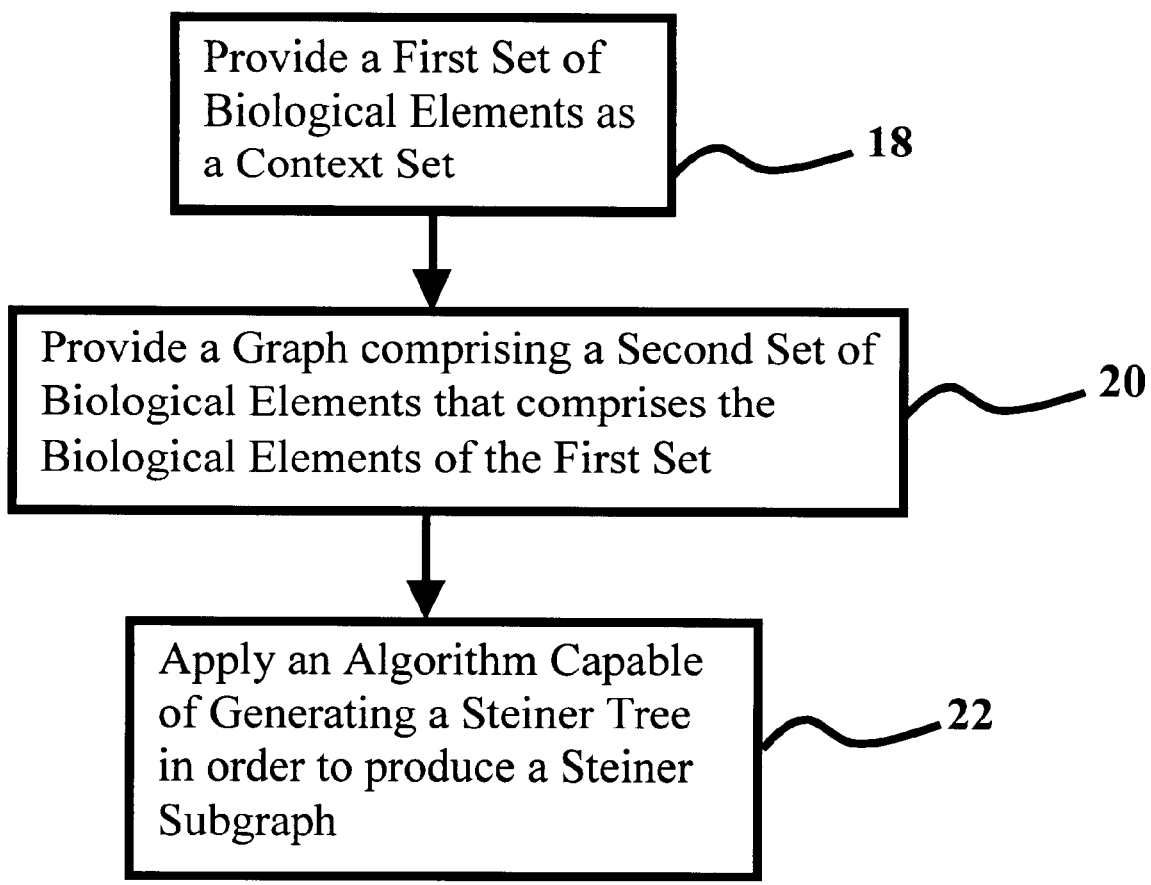
FIG. 2 is a flow diagram of one embodiment of a method of the present invention.

FIG. 2 is a flow diagram of one embodiment of a method of the present invention for determining the associations of a set of biological elements through the analysis of a graph of biological elements with defined biorelationships. As used herein, a "biorelationship" is any observed or defined relationship between two biological elements. The relationship can be an actual observed molecular interaction, such as a substrate and enzyme relationship or a protein and DNA relationship. The relationship can also be any relationship that is definable by a researcher, such as nucleic acid sequence homology or protein domain homology. Examples of biorelationships include, without limitation, a genetic interaction between two genes, a protein—protein interaction between the products of the two genes, a conserved domain in the sequence of two genes, the co-occurrence or lack thereof of genes in a transcript profiling cluster, substrate and enzyme interactions, enzymatic pathway components, nucleic acid sequence homology, protein sequence homology, the co-occurrence of proteins in a translation profiling cluster, protein-DNA binding, protein domain homology, and signaling pathway interactions, among others. In one embodiment, the biorelationships are selected from the group consisting of a genetic interaction between two genes, a protein-protein interaction between the products of the two genes, a conserved domain in the sequence of two genes, and the co-occurrence of genes in a transcript profiling cluster.

As used herein, a "gene" is a nucleic acid sequence or portion thereof that encodes a protein. Nucleic acid sequences include, without limitation, DNA in any form, such as genomic DNA, cDNA, synthesized DNA. Nucleic acid sequences also include RNA and RNA transcripts corresponding to the DNA described above.

As used herein, a "biological element" is any physical entity or component of a biological system or anything that interacts or affects a biological system. A biological element can be, for example and without limitation, an atomic particle, an atom, molecule, compound, or combination thereof, including cellular organisms. A biological system can be any living organism, virus, cell, or components derived therefrom. In a preferred embodiment, biological elements comprise genes. In another preferred embodiment, biological elements comprise enzymes. In a further preferred embodiment, biological elements comprise enzymes and enzyme substrates and products. In yet another preferred embodiment, biological elements comprise genes and enzymes.

As used herein, a "set of biological elements" or "set of genes" can be any form of representation of biological elements or genes that can be inputted into an algorithm being applied. Representations include numerical and symbolic forms, such as numbers and letters. In a preferred embodiment, representations are numbers.

As shown in step 18 of FIG. 2, a First Set of biological elements is provided as a Context Set. This set can be any set of biological elements. The biological elements can be chosen for the set based on no specific prior knowledge about the potential associations, or they can be chosen because they have been determined to have potential associations. For example, the Context Set can comprise genes that were determined to be upregulated during a single transcription profiling experiment. In this case, it would have been determined that the genes in the Context Set are all upregulated in response to the experimental variable introduced in the experiment. Having knowledge of their contemporaneous upregulation, a researcher would provide a Context Set with the upregulated genes for examination in the method.

Figure 1:
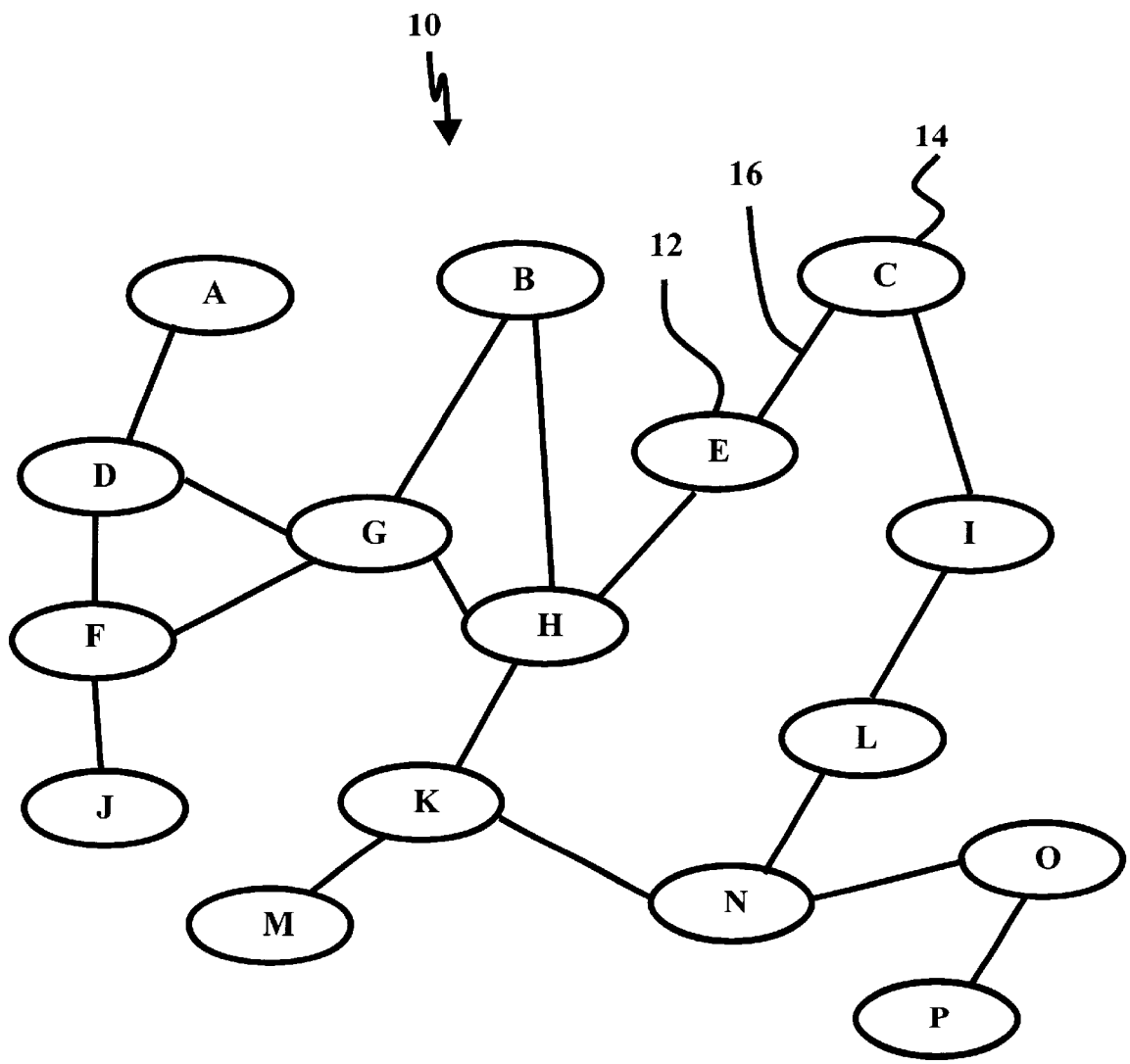
FIG. 1 is a graph of a hypothetical simple network of vertices and edges.

In step 20, a graph representing biorelationships of a second set of biological elements, where the second set of biological elements comprises the biological elements of the Context Set, is provided. Step 18 and step 20 can be reversed in order. As used herein, a "graph" is any representation of a set of biological elements and the biorelationships among them. A graph can be a representation of a single database of biorelationships or a representation of biorelationships that includes more than one such database. In an embodiment where a graph comprises more than one database, the multiple databases are each connected to at least one of the other databases by at least one biorelationship. A graph can be in viewable form, such as the graph shown in FIG. 1, as well as any digital or other representation of the viewable form, such as the actual digital code that is used by a software program to create the viewable form of the graph. Graphs can also be represented, for example, as a series of numbers representing the biological elements and the biorelationships among them. For example, the graph can be encoded as a matrix of three number groups, with each group of three numbers representing three biological elements. In this configuration, a biorelationship exists between the first and second biological elements, and the second and third biological elements. Graphs can be, for example, those found in the Kyoto Encyclopedia of Genes and Genomes and those presented in the literature (see, for example, Eisenberg et al., Protein Function in the Post-Genomic Era, Nature, Volume 405, Number 6788, Pages 823–826 (2000), and Uetz et al., A Comprehensive Analysis of Protein—Protein Interactions in *Saccharomyces cerevisiae*, Nature, Volume 403, Number 6770, Page 623–627 (2000)). A graph comprises vertices and edges. As used herein, a "vertex" is a representation in a graph of a biological element and an "edge" is a representation in a graph of a biorelationship between two vertices. In one embodiment, the graph has only one type of vertex and one type of edge. For example, the vertices could be enzymes and the edges could represent the biorelationship of two enzymes where the first enzyme catalyzes the formation of a product which is the substrate for the second enzyme. In another embodiment, vertices can represent both the enzymes and the substrates and products of the enzymes, and the edges represent the substrate-enzyme biorelationship. In another embodiment, either the vertices, the edges, or both are of a different type. For example, the vertices can represent genes, and the edges can represent either sequence homology between two genes or product/substrate equivalency between the enzymes encoded by two genes (i.e. the product of an enzyme encoded by one gene is the substrate of an enzyme encoded by another gene). FIG. 1 is a schematic representation of a simple graph shown generally at 10, with vertices lettered A through P, and edges, which are shown as straight lines connecting the vertices.

The graph provided in step 20 of FIG. 2 can contain as vertices all of the biological elements of the Context Set. As an illustration, a Context Set could comprise the biological elements F, C, and K, and the graph could be the graph shown in FIG. 1. In this illustration the Context Set has three biological elements—F, C, and K—and the graph contains each of them. In one embodiment, the method removes biological elements in the Context Set if those elements are not represented by vertices in the graph. After step 20 is completed, a Context Set comprising the biological elements of interest and a graph containing vertices representing a second set of biological elements comprising the biological elements of the Context Set have been provided.

In step 22, an algorithm capable of generating a Steiner Tree is applied to the graph to find the edges and vertices of the graph that connect the vertices representing the biological elements in the Context Set. As used herein, "applying an algorithm capable of generating a Steiner Tree" means inputting data into an algorithm and outputting a result of that algorithm. As used herein, an "algorithm capable of generating a Steiner Tree" is any algorithm that is capable of taking as inputs a Context Set and a graph and producing as an output one or more Steiner Trees for the vertices in the graph that represent the Context Set, whether or not the resulting Steiner Tree or Steiner Trees are the most efficient. More than one Steiner Tree solution can be generated by the algorithm if, for example, multiple Steiner Trees are equivalent solutions (that is, they have the same efficiency). Examples of algorithms that are capable of generating a Steiner Tree include the shortest path heuristic, the minimum spanning tree heuristic, the distance network heuristic, and the simulated annealing heuristic (Rayward-Smith and Clare, On Finding Steiner Vertices, Networks 16, 283–294 (1986), Takahashi and Matsuyama, An Approximate Solution for the Steiner Problem in Graphs, Math. Jap. 24, 573–577 (1980), Choukhmane, Une Heuristique Pour le Probleme de L'arbre de Steiner, RAIRO Rech. Oper. 12, 207–212 (1978), Schiemanek, Thermodynamically Motivated Simulations for Optimization of Interacting Path Systems, Optimization of Connection Structures in Graphs, Iwainski (editor), CICIP, East Berlin, GDR pages 74–90 (1985), Hwang, The Steiner Tree Problem, Amsterdam, New York, North-Holland (1992), all of which are herein incorporated by reference in their entirety). In a preferred embodiment, the algorithm is a minimum spanning tree heuristic.

Algorithms that are capable of generating a Steiner tree have been used to determine, for example, the most efficient connections between components on an integrated circuit device. Such an application helps microchip engineers to determine the most efficient use of space on a semiconductor device on which space is of significant concern.

As used herein, a "Steiner Tree" is the most efficient connection of the vertices in the graph that correspond to the Context Set as determined by the algorithm being used. That is, the solution generated by an algorithm is, as used herein, a Steiner Tree, even if that solution is not the most efficient connection of the vertices in the graph that correspond to the Context Set. As used herein, the "most efficient" connection of vertices means the set of edges and vertices that use either the fewest edges possible or the edges with the least total edge weight to connect the vertices in the graph that correspond to the Context Set as determined by the algorithm. In either case, the Steiner Tree will be connected, contain no cycles, and the ends of the Steiner Tree will each correspond to a member of the Context Set.

The output of the algorithm is a Steiner subgraph. As used herein, a "Steiner subgraph" is the output of an algorithm capable of generating a Steiner Tree, where the output comprises a Steiner Tree or multiple overlayed Steiner Trees. In one embodiment, the Steiner subgraph is a single Steiner Tree. In another embodiment, the Steiner subgraph is a combination of different overlayed Steiner Trees all having the same number of edges or the same weight (that is, they are equivalently efficient). In this embodiment, the Steiner subgraph produced comprises all of the vertices and edges of each of the Steiner Tree solutions generated by the algorithm.

Figure 3:
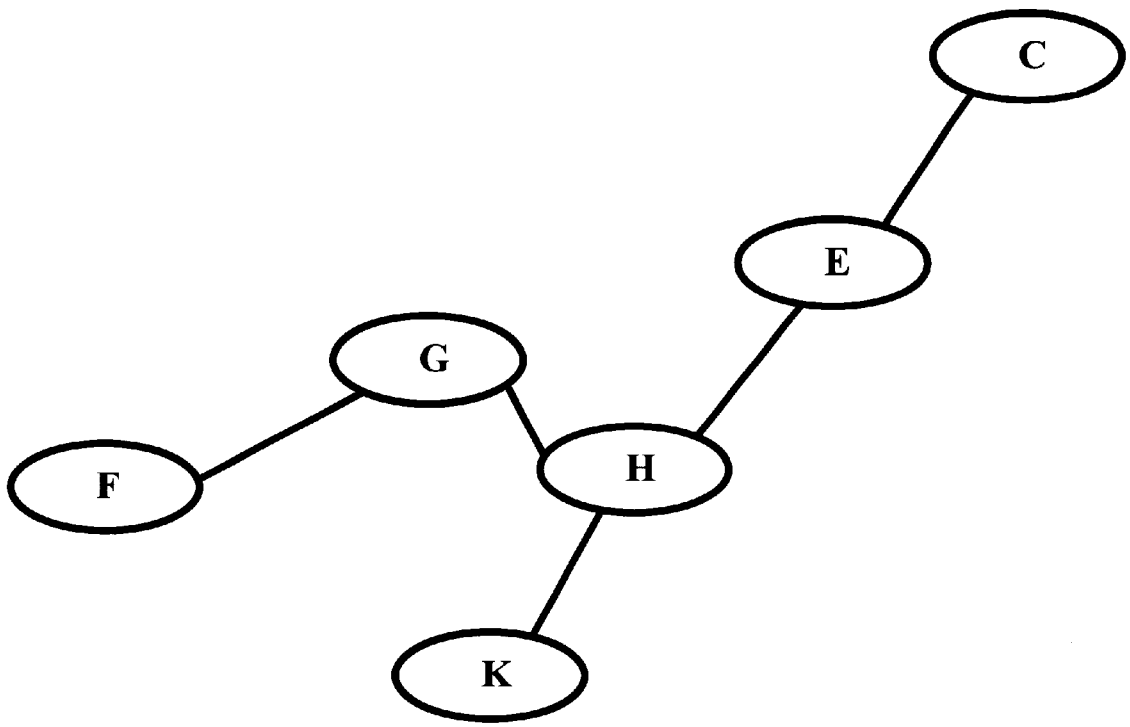
FIG. 3 is an illustration of a Steiner tree solution to the graph shown in FIG. 1.

Applying the flow diagram shown in FIG. 2 to the illustration given above, the following steps are performed. In step 18, the First Set (Context Set) of biological elements is provided. The Context Set has as members F, C, and K. In step 20, the graph shown in FIG. 1 is provided. The graph in FIG. 1 represents a second set of biological elements and contains as vertices the members of the Context Set, F, C, and K. In step 22, an algorithm capable of generating a Steiner Tree is applied to the graph and the Context Set. The Steiner subgraph produced by the illustration is shown in FIG. 3. FIG. 3 shows a Steiner subgraph comprising the three vertices corresponding to the biological elements of the context set (F, C, and K), edges, and the additional vertices (E, G, and H, which are known as Steiner vertices, because they are members of the Steiner Tree but not of the Context Set) determined by the algorithm to form the Steiner Tree solution. The illustrative Steiner subgraph in FIG. 3 is the single most efficient Steiner Tree solution because it has the fewest number of edges required to connect all of the vertices of the graph that correspond to the biological elements of the First Set. In this illustration, all edges have the same value (that is, they are all of equal weight), which means that the most efficient Steiner Tree solution has the fewest number of edges.

The process as described above allows for the rapid identification of biological elements that potentially are associated with or connect members of the Context Set. In the illustration, for example, the algorithm determined that the most efficient Steiner Tree included biological elements E, G, and H. From this information, a researcher would be able to quickly focus in on likely biological elements that could be associated with the Context Set. For example if an RNA transcript profiling experiment indicated that biological elements F, C, and K were upregulated together, then a researcher could examine biological elements E, G, and H for evidence that they are somehow associated with that upregulation. The power of this method is readily apparent; whereas conventional methods depend on known pathways and are therefore restricted to returning known pathway information, the present invention allows for the determination of associations among biological elements that have not been previously recognized as belonging in a pathway or group.

In an alternative embodiment, edges can be weighted to represent relative biorelationships. Weight can be assigned for any reason, with a greater weight signifying a less preferred biorelationship. Weight can be assigned, for example and without limitation, according to the certainty of the biorelationship, the degree of molecular binding, and the extent of homology, among others. In an embodiment in which edges are assigned differential weights, the algorithm capable of generating a Steiner Tree generates a Steiner Tree comprising edges having the lowest possible sum of weights as determined by the algorithm.

Figure 4:
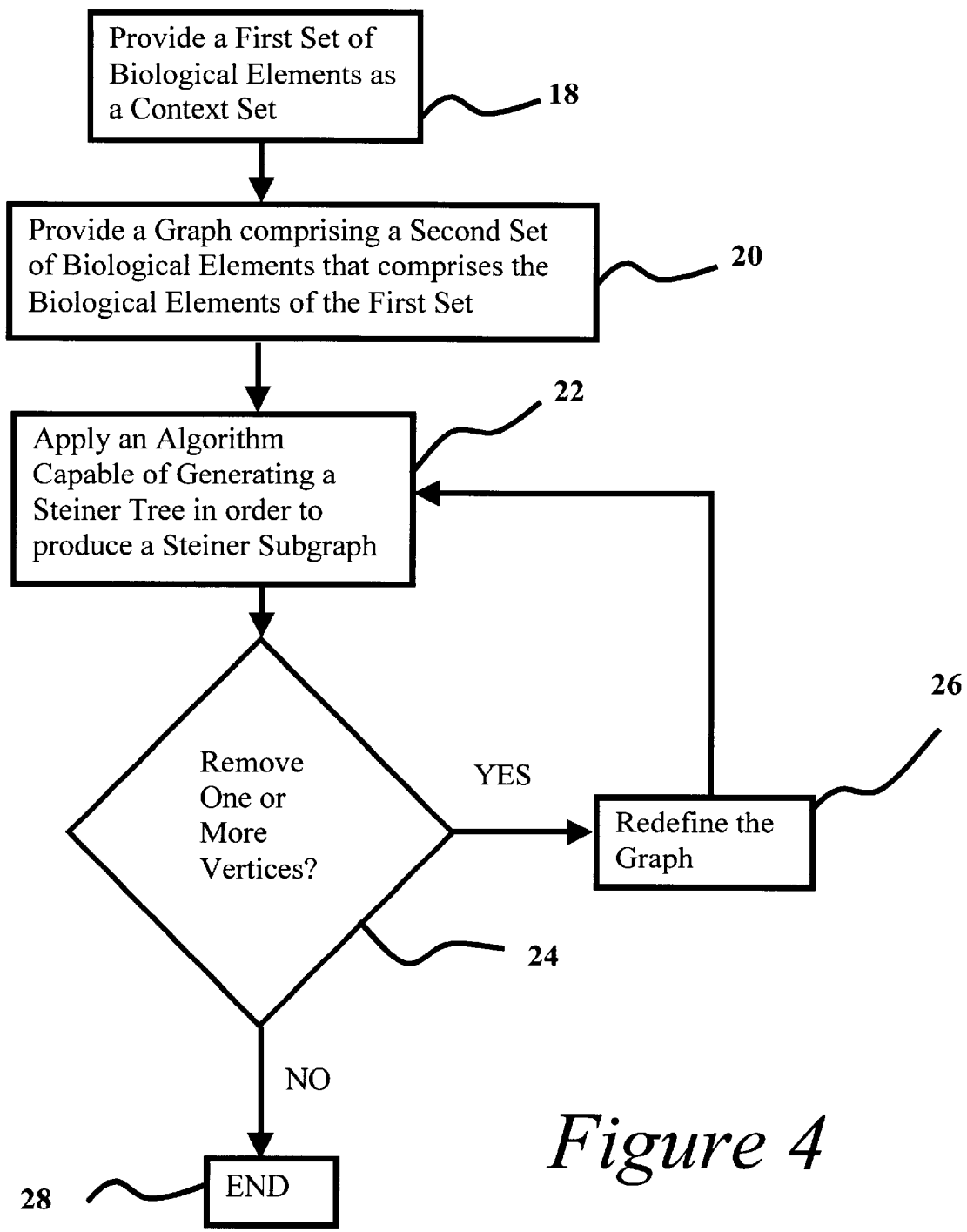
FIG. 4 is a flow diagram of one embodiment of a method of the present invention in which vertices can be iteratively removed.

FIG. 4 shows a flow diagram of one embodiment of the present invention in which a graph can be altered to allow for flexibility in generating a Steiner subgraph. In this embodiment, steps 18, 20, and 22 are performed as before (steps 18 and 20 can be performed in reverse order), and then flow proceeds to step 24. In step 24, the question is asked if, based on the Steiner subgraph produced in step 22 or otherwise, vertices should be removed from the graph. The purpose of this question is to allow for removal of vertices that are not deemed relevant enough but which are found in the Steiner Tree; by removing unwanted vertices, the algorithm will be forced to find a Steiner Tree solution that does not use the removed vertices. If in step 24 the answer to the prompt is yes, then flow proceeds to step 26, where the graph is redefined to exclude unwanted vertices. Flow then proceeds to step 22, where the algorithm is again applied, but now on the redefined graph and the original Context Set supplied in step 18. If in step 24 the answer to the prompt is no, then flow proceeds to step 28 and ends. This embodiment allows an investigator to examine Steiner subgraphs for vertices that they find uninteresting, and then to remove those vertices. Vertices with large numbers of edges, such as water or adenosine triphosphate (ATP), can be removed from the graph to allow the algorithm to generate alternative Steiner Trees.

Figure 5:
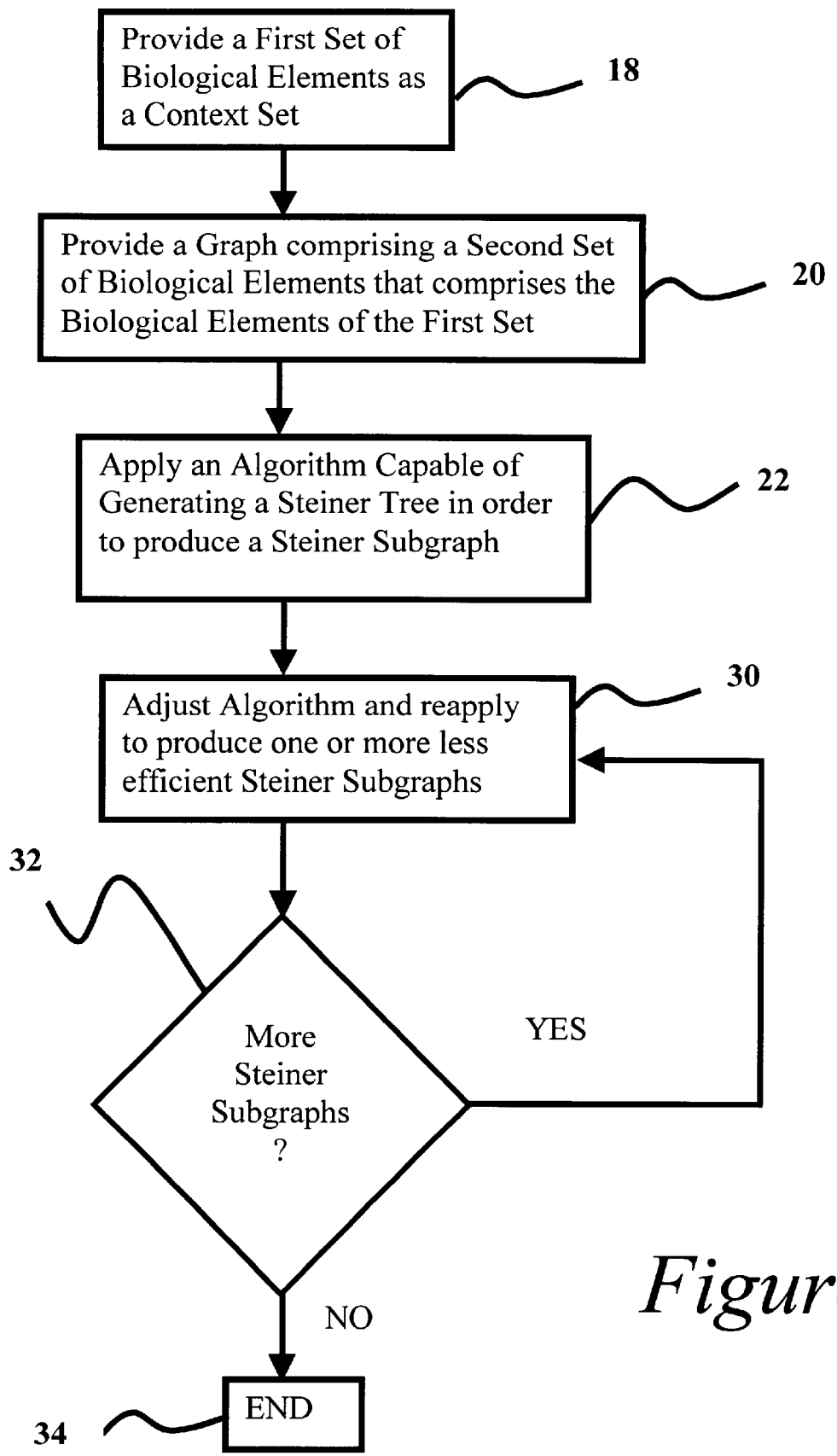
FIG. 5 is a flow diagram of one embodiment of a method of the present invention in which broadened results can be generated.

FIG. 5 shows a flow diagram of one embodiment of the present invention in which an algorithm can be adjusted to produce less efficient Steiner Trees. Steps 18, 20, and 22 are performed as before (steps 18 and 20 can be performed in reverse order), and then flow proceeds to step 30. At step 30, the algorithm is adjusted to produce one or more less efficient Steiner subgraphs than the one produced in step 22. In one embodiment, adjustment can entail removing vertices from the graph and rerunning the algorithm. In another embodiment, the algorithm is restricted to returning Steiner trees that are less efficient than the Steiner Tree produced in step 22 but more efficient than an edge number or weight assigned by the investigator. As used herein, "less efficient" means a Steiner tree having relatively more edges or greater total edge weight. In step 32, the question is asked if more Steiner subgraphs are desired. If answered yes, flow returns to step 30, where the algorithm can again be adjusted to produce an even less efficient Steiner subgraph. If in step 32 the question is answered no, then flow proceeds to step 34 and ends.

Implementation

Figure 6:
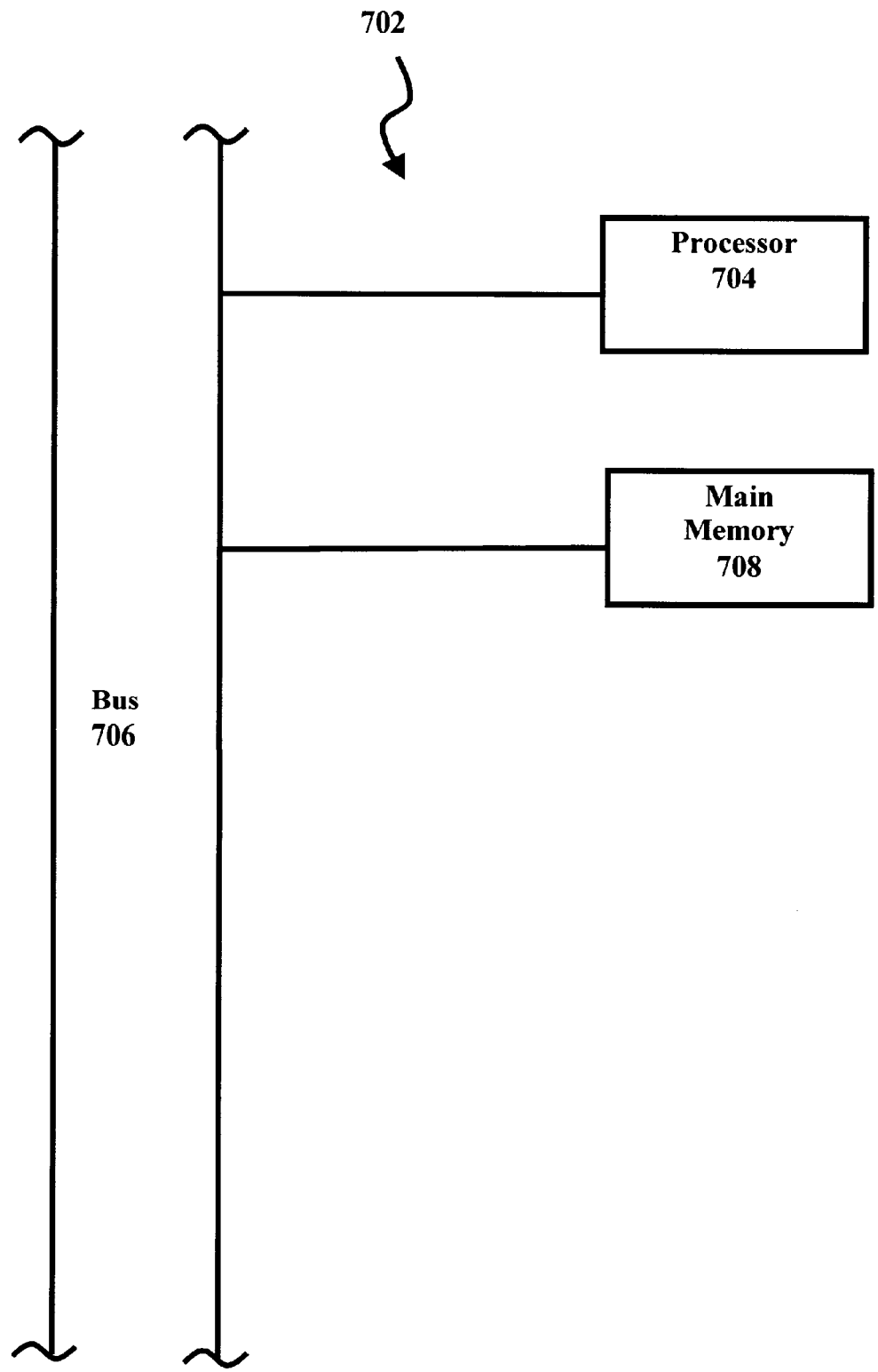
FIG. 6 is a schematic representation of one embodiment of a computer system.

A computer system capable of carrying out the functionality and methods described above is shown in more detail in FIG. 6. A computer system 702 includes one or more processors, such as a processor 704. The processor 704 is connected to a communication bus 706. The computer system 702 also includes a main memory 708, which is preferably random access memory (RAM). Various software embodiments are described in terms of this exemplary computer system. After reading this description, it will become apparent to a person skilled in the relevant art how to implement the invention using other computer systems and/or computer architectures.

Figure 7:
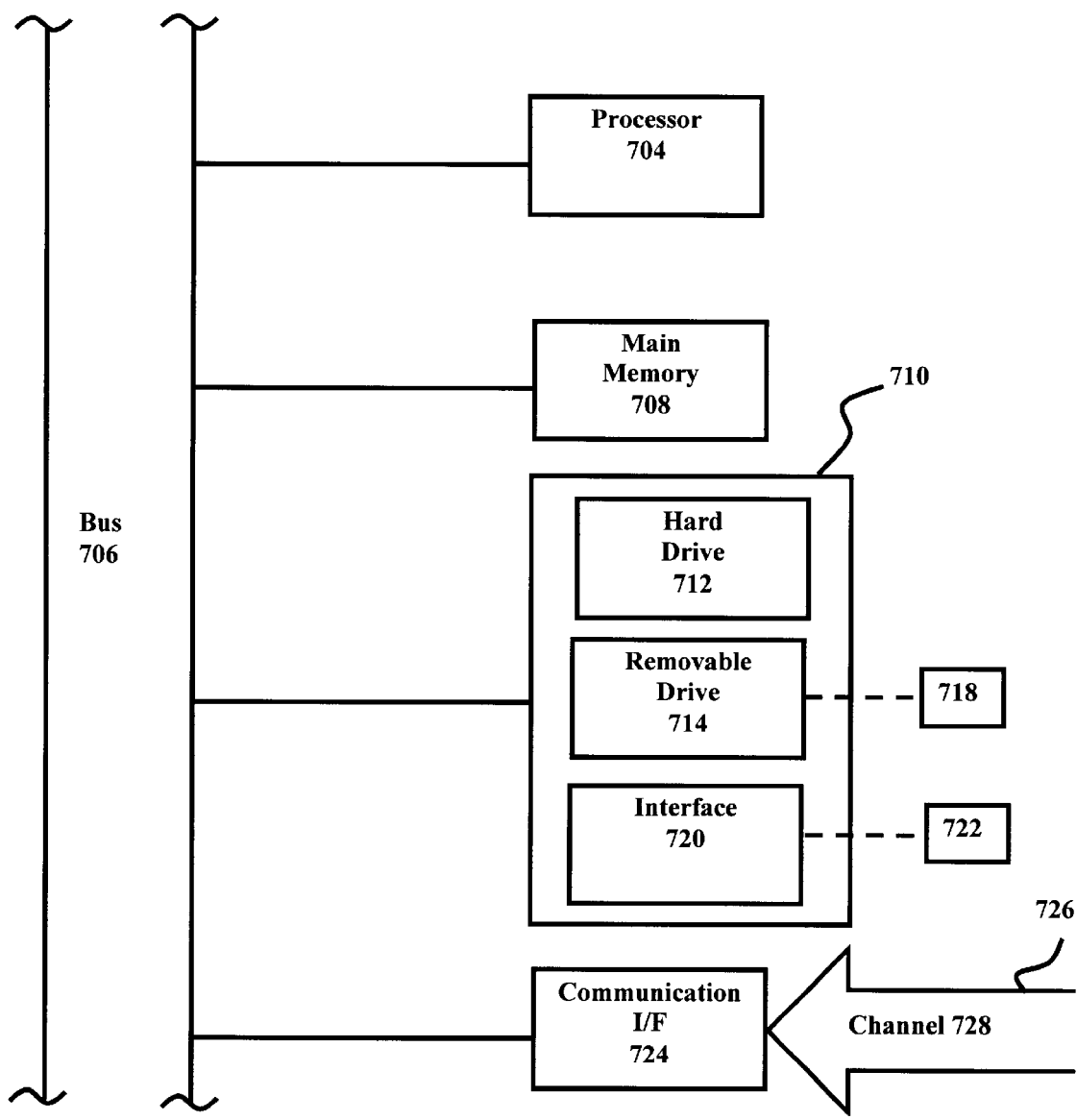
FIG. 7 is a schematic representation of one embodiment of a computer system.

In a further embodiment, shown in FIG. 7, the computer system can also include a secondary memory 710. The secondary memory 710 can include, for example, a hard disk drive 712 and/or a removable storage drive 714, representing a floppy disk drive, a magnetic tape drive, or an optical disk drive, among others. The removable storage drive 714 reads from and/or writes to a removable storage unit 718 in a well known manner. The removable storage unit 718, represents, for example, a floppy disk, magnetic tape, or an optical disk, which is read by and written to by the removable storage drive 714. As will be appreciated, the removable storage unit 718 includes a computer usable storage medium having stored therein computer software and/or data.

In alternative embodiments, the secondary memory 710 may include other similar means for allowing computer programs or other instructions to be loaded into the computer system. Such means can include, for example, a removable storage unit 722 and an interface 720. Examples of such can include a program cartridge and cartridge interface (such as that found in video game devices), a removable memory chip (such as an EPROM, or PROM) and associated socket, and other removable storage units 722 and interfaces 720 which allow software and data to be transferred from the removable storage unit 722 to the computer system.

The computer system can also include a communications interface 724. The communications interface 724 allows software and data to be transferred between the computer system and external devices. Examples of the communications interface 724 can include a modem, a network interface (such as an Ethernet card), a communications port, a PCMCIA slot and card, etc. Software and data transferred via the communications interface 724 are in the form of signals 726 that can be electronic, electromagnetic, optical or other signals capable of being received by the communications interface 724. Signals 726 are provided to communications interface via a channel 728. A channel 728 carries signals 726 in two directions and can be implemented using wire or cable, fiber optics, a phone line, a cellular phone link, an RF link and other communications channels. In one embodiment, the channel is a connection to a network. The network can be any network known in the art, including, but not limited to, LANs, WANs, and the Internet. Biological element or biorelationship data can be stored in remote systems, databases, or distributed databases, among others, for example GenBank, and transferred to computer system for processing via the network. In one embodiment, biological element data and biorelationship data is received through the Internet via the channel 728. Sequence data can be input into the system and stored in the main memory 708. Input devices include the communication and storage devices described herein, as well as keyboards, voice input, and other devices for transferring data to a computer system.

In this document, the terms "computer program medium" and "computer usable medium" are used to generally refer to media such as the removable storage device 718, a hard disk installed in hard disk drive 712, and signals 726. These computer program products are means for providing software to the computer system.

Computer programs (also called computer control logic) are stored in the main memory 708 and/or the secondary memory 710. Computer programs can also be received via the communications interface 724. Such computer programs, when executed, enable the computer system to perform the features of the present invention as discussed herein. In particular, the computer programs, when executed, enable the processor 704 to perform the features of the present invention. Accordingly, such computer programs represent controllers of the computer system.

In an embodiment where the invention is implemented using software, the software may be stored in a computer program product and loaded into the computer system using the removable storage drive 714, the hard drive 712 or the communications interface 724. The control logic (software), when executed by the processor 704, causes the processor 704 to perform the functions of the invention as described herein.

In another embodiment, the invention is implemented primarily in hardware using, for example, hardware components such as application specific integrated circuits (ASICs). Implementation of such a hardware state machine so as to perform the functions described herein will be apparent to persons skilled in the relevant art(s). In yet another embodiment, the invention is implemented using a combination of both hardware and software.

The following examples are illustrative only. It is not intended that the present invention be limited to the illustrative embodiments.

EXAMPLE 1

In this example a Steiner subgraph is produced from the output of an algorithm capable of generating a Steiner Tree. The program used to apply the algorithm used in this example is a script that is written in MATLAB (The MathWorks, 3 Apple Hill Drive, Natick, Mass. 01760-2098) that is named pathmap.m. Lines that indicate programmer comments begin with a "%" sign. As used in the comments, "targets" are the members of the Context Set. Pathmap.m is shown below:

```
clear ;
% This is the context set.
load targets.txt ;
% This is the deletion set.
load rejections.txt ;
% This is information about G_bio, which is the graph in this example.
nodes = readstrings ('keggNodes.txt') ;
formulas = readstrings ('keggFormulas.txt') ;
% This is G_bio.
load keggGraph.txt ;
% If there are four arguments the fourth one is ignored and simply
% used as a flag to tell us that subgraphs showing the detailed enzymatic
% details should *not* be generated for each edge in the graph . . .
[unused, targetSize] = size (targets) ;
if targetSize == 4
    subgraph = 0 ;
```

```
else
    subgraph = 1 ;
end
% Number of edge entries.
[entryNum notUsed] = size (keggGraph) ;
% Largest nodeID
maxEntry = max (max (keggGraph)) ;
% Build sparse matrix representation of the metabolic graph.
kegg =
sparse (keggGraph (:, 2) , keggGraph (:, 3) , ones (entryNum,1) , maxEntry,maxEntry) ;
kegg = spones (kegg) ;
% Ensure that it is symmetric.
kegg = spones (kegg + kegg' + speye (maxEntry)) ;
% Simple sanity check.
[nodeNum nodeNum2] = size (kegg) ;
if nodeNum~ = nodeNum2
    error ('Something is wrong with your KEGG . . . \n') ;
end
% Remove substrates with highest order (e.g. H20, ATP, ADP etc.)
[vals index] = sort (sum (kegg)) ;
index = index (end:-1:1) ;
for i = index (1:14)
    kegg (i, :) = zeros (1, maxEntry) ;
    kegg (:, i) = zeros (maxEntry, 1) ;
end
for i = rejections
    kegg (i, :) = zeros (1, maxEntry) ;
    kegg (:, i) = zeros (maxEntry, 1) ;
end
% Since this implements the N = 3 Heuristic we can actually give
% the targets a name . . . chosen from the example being studied.
glucose = targets (1) ;
ethanol = targets (2) ;
threonine = targets (3) ;
% Important Note: the current implementation assumes that the
% targets are all members of the same connected component.
% Calculate the distance matrix from every target to every other
% node in the graph.
distanceGlucose = dijkstra (kegg, glucose) ;
distanceThreonine = dijkstra (kegg, threonine) ;
distanceEthanol = dijkstra (kegg, ethanol) ;
% Calculate total distance from any given node to all three targets.
totalDistance = distanceGlucose + distanceThreonine + distanceEthanol ;
% Find those points which minimize total distance to target.
% The N = 3 Heuristic is based on the insight that these special
% points are the 'centers' of valid minimal Steiner Trees.
steinerSpecialPoints = find (totalDistance == min (totalDistance)) ;
% Important Note: rather than pick one steiner tree as the solution
% to the problem, this implementation displays them all.
% Start generating output file . . .
file = fopen ('SteinerGraph.gdl', 'w') ;
% General graph rendering properties . . .
fprintf (file, 'graph: {\n') ;
fprintf (file, ' display_edge_labels: yes\n') ;
fprintf (file, ' hidden: 2\n') ;
%fprintf (file, ' smanhattan edges: yes\n') ;
fprintf (file, ' splines: yes\n') ;
fprintf (file, ' splinefactor: 50\n') ;
fprintf (file, ' layoutalgorithm: maxdepthslow\n') ;
%fprintf (file,' edge.arrowstyle: none\n') ;
% Generate the output file, while keeping track of which nodes and
% edges were visited.
steinerNodes = zeros (1, nodeNum) ;
steinerEdges = sparse (nodeNum, nodeNum) ;
additionalNodes = nodeNum + 1 ;
for i = steinerSpecialPoints
    [steinerNodes, steinerEdges, additionalNodes] =
traceBack (i, subgraph, additionalNodes, distanceGlucose, steinerNodes, steinerEdges
, kegg, nodes, formulas, keggGraph, file) ;
    [steinerNodes, steinerEdges, additionalNodes] =
traceBack (i, subgraph, additionalNodes, distanceThreonine, steinerNodes, steinerEdg
es, kegg, nodes, formulas, keggGraph, file) ;
    [steinerNodes, steinerEdges, additionalNodes] =
traceBack (i, subgraph, additionalNodes, distanceEthanol, steinerNodes, steinerEdges
, kegg, nodes, formulas, keggGraph, file) ;
end
% End of output file . . .
fprintf (file,')\n') ;
fclose (file) ;
```

-continued

Pathmap.m calls two functions, dijkstra.m and traceBack.m, which are produced below:

```
function distanceFromNode = dijkstra (graph, node)
% This function is used to calculate distances from every
% node in the graph to a given target node. The function
% is called by the implementation of Steiner Tree extraction
% (N = 3 Heuristic) as coded in the file pathmap.m
[nodes1 nodes2] = size (graph) ;
if nodes1 ~= nodes2
    error ('Invalid graph matrix! ') ;
end
distance = 0 ;
distanceFromNode = ones (1, nodes1) .* (2*nodes1) ;
distanceFromNode (node) = distance ;
frontNodes = zeros (nodes1, 1) ;
frontNodes (node) = 1 ;
while 1 > 0
    fN2 = spones (graph*frontNodes) ;
        if nnz (fN2) == nnz (frontNodes)
            break ;
        end
        distance = distance + 1 ;
        size (find(fN2 - frontNodes)) ;
        distanceFromNode (find(fN2 - frontNodes)) = distance ;
    frontNodes = fN2 ;
end
```

And the second function, traceBack.m:

```
function [steinerNodes, steinerEdges, additionalNodes] =
traceBack (i, subgraph, additionalNodes, distances, steinerNodes, steinerEdges, kegg,
nodes, formulas, keggGraph, file)
% This function is used to generate the output file for the
% implementation of Steiner Tree extraction (N = 3 Heuristic)
% as coded in the file pathmap.m
if steinerNodes (i) == 0
    steinerNodes (i) = 1 ;
        if distances (i) == 0
        fprintf (file, 'node: {bordercolor: red shape: ellipse title: "%d" label:
"%s" \n', i , nodes {i}) ;
        else
        fprintf (file, 'node: {title: "%d" label: "%s" infol:
"%d" }\n', i, nodes {i},i) ;
        end
end
if (distances (i) ~= 0)
    neighbours = find (kegg (i, :)) ;
    closerNeighbours = find (distances (neighbours) < distances (i)) ;
    for j = neighbours (closerNeighbours)
        if steinerEdges (i, j) == 0
            steinerEdges (i, j) = 1 ;
                steinerEdges (j, i) = 1 ;
                entries = size (keggGraph) ;
                if subgraph == 1
                    fprintf (file,'graph: { title: "%s" label: "%s" status:
folded\n', additionalNodes*1000, strcat (nodes {i }, '<->', nodes {j})) ;
                    from = additionalNodes*1000+1 ;
                    to = additionalNodes*1000+2 ;
        fprintf (file, ' node: { label: "" color: green scaling: 0.1 shape:
circle title: "%d"}\n', from) ;
        fprintf (file, ' node: { label: "" color: green scaling: 0.1 shape:
circle title: "%d"}\n', to) ;
                        fprintf (file, ' edge: { arrowstyle: none class: 1
sourcename: "%d" targetname: "%d"}\n', i, j) ;
                        fprintf (file, ' edge: { arrowstyle: none class: 2
sourcename: "%d" targetname: "%d"}\n', i, from) ;
                        fprintf (file, ' edge: { arrowstyle: none class: 2
sourcename: "%d" targetname: "%d"}\n', to, j) ;
                        for k=1:entries
                            if (keggGraph (k, 2) == i) & (keggGraph ( k, 3) == j)
            fprintf (file,' node: {bordercolor: blue shape: hexagon title:
"%d" label: "%s" infol: "%s"
}\n', additionalNodes, nodes {keggGraph (k, 1) }, formulas {k}) ;
                            fprintf (file, 'edge: { color: purple class: 2
sourcename: "%d" targetname: "%d"}\n', from, additionalNodes) ;
                            fprintf (file, ' edge: { color: purple class: 2
sourcename: "%d" targetname: "%d"}\n', additionalNodes, to) ;
                                additionalNodes = additionalNodes + 1 ;
                            end
                        end
```

```
                for k = 1:entries
                    if (keggGraph (k, 2) == j) & (keggGraph (k, 3) == i)
            fprintf (file, ' node: {bordercolor: blue shape: hexagon title:
"%d" label: "%s" infol: "%s"
}\n', additionalNodes, nodes {keggGraph (k, 1) }, formulas {k}) ;
                    fprintf (file, ' edge: { linestyle: dashed color: purple
class: 2 sourcename: "%d" targetname: "%d"}\n', to, additionalNodes) ;
                    fprintf (file, ' edge: { linestyle: dashed color
purple class: 2 sourcename: "%d" targetname: "%d"}\n', additionalNodes, from) ;
                        additionalNodes = additionalNodes + 1 ;
                end
            end
            fprintf (file,'}\n') ;
        else
            fprintf (file,' edge: { arrowstyle: none class: 1
sourcename: "%d" targetname: "%d"}\n', i, j) ;
                for k = 1:entries
                    if (keggGraph (k, 2) == i) & (keggGraph (k, 3) == j)
            fprintf (file, ' node: (bordercolor: blue shape: hexagon title:
"%d" label: "%s" infol: "%s"
}\n', additionalNodes, nodes {keggGraph (k, 1) }, formulas {k}) ;
                    fprintf (file, ' edge: { color: purple class: 2
sourcename: "%d" targetname: "%d"}\n', i, additionalNodes) ;
                    fprintf (file, ' edge: { color: purple class: 2
sourcename: "%d" targetname: "%d"}\n', additionalNodes, j) ;
                        additionalNodes = additionalNodes + 1 ;
                end
            end
                for k = 1:entries
                    if (keggGraph (k, 2) == j) & (keggGraph (k, 3) == i)
            fprintf (file, ' node: {bordercolor: blue shape: hexagon title:
"%d" label: "%s" infol: "%s"
}\n', additionalNodes, nodes {keggGraph(k, 1) }, formulas {k}) ;
                    fprintf (file, ' edge: { linestyle: dashed color: purple
class: 2 sourcename: "%d" targetname: "%d"}\n', j, additionalNodes) ;
                    fprintf (file, ' edge: { linestyle: dashed color:
purple class: 2 sourcename: "%d" targetname: "%d"}\n', additionalNodes, i) ;
                        additionalNodes = additionalNodes + 1 ;
                end
            end
        end
    end
    [steinerNodes, steinerEdges, additionalNodes] =
traceBack (j, subgraph, additionalNodes, distances, steinerNodes, steinerEdges, kegg,
nodes, formulas, keggGraph, file) ;
    end
end
```

Pathmap.m has the following inputs, the first three of which are approximately equivalent to the pathways present in *Saccharomyces cerevisiae* and *Saccharomyces pombe* in KEGG:

Input 1: The file keggNodes.txt (not shown), which contains the names of the vertices of the graph. Every vertex has the implicit ID of the line number on which it is found, and there are hundreds of vertices. Sample lines from keggNodes.txt are as follows:

Bialaphos
2-Hydroxyethylamine
N-Trimethyl-2-aminoethylphosphonate
Leukotriene F4
1.1.1.1
1.1.1.2
1.1.1.27
1.1.1.71 where the named compounds represent either substrates or products, and the numbers represent standard numerical numbering for enzymes.

Input 2: The file keggGraph.txt (not shown), which is a matrix comprising groups of three numbers. Each group of three numbers corresponds to the identity of three nodes, where the first number represents an enzyme, the second number represents a substrate of the enzyme, and the third number represents a product of the enzyme. Edges exist conceptually between the first and second, and the first and third nodes. An example of groups in the file is shown below:

2623 25 4
2623 25 26
2623 25 59
2625 3 4

Input 3: The file keggFormulas.txt (not shown), which comprises textual representations from which the entries in keggGraph are extracted. An example of the entries in keggFormulas.txt is as follows:

1 2,5-Dihydroxybenzoate+1 NADH<=>1 Gentisate aldehyde+1 H2O+1 NAD+
1 Oxygen+1 2,5-Dihydroxybenzoate<=>1 Maleylpyruvate
1 Oxygen+1 2,5-Dihydroxybenzoate<=>1 Maleylpyruvate
1 2,5-Dihydroxybenzoate+1 H2O2 <=>1 Oxygen+1 Gentisate aldehyde+1 H2O Input 4: The file targets.txt, which comprises the actual members of the Context Set listed by their line number in keggNodes. The actual file is shown below:

31 168 353

The three numbers represent the biological elements of D-Glucose, L-Threonine, and Ethanol.

Input 5: The file rejections.txt, which comprises the vertices of the graph that are to be ignored by the algorithm when generating a Steiner Tree. The actual file is shown below:

27 30 15 28 432 114 469 1386 113 288 971 124 91 125

Figure 8:
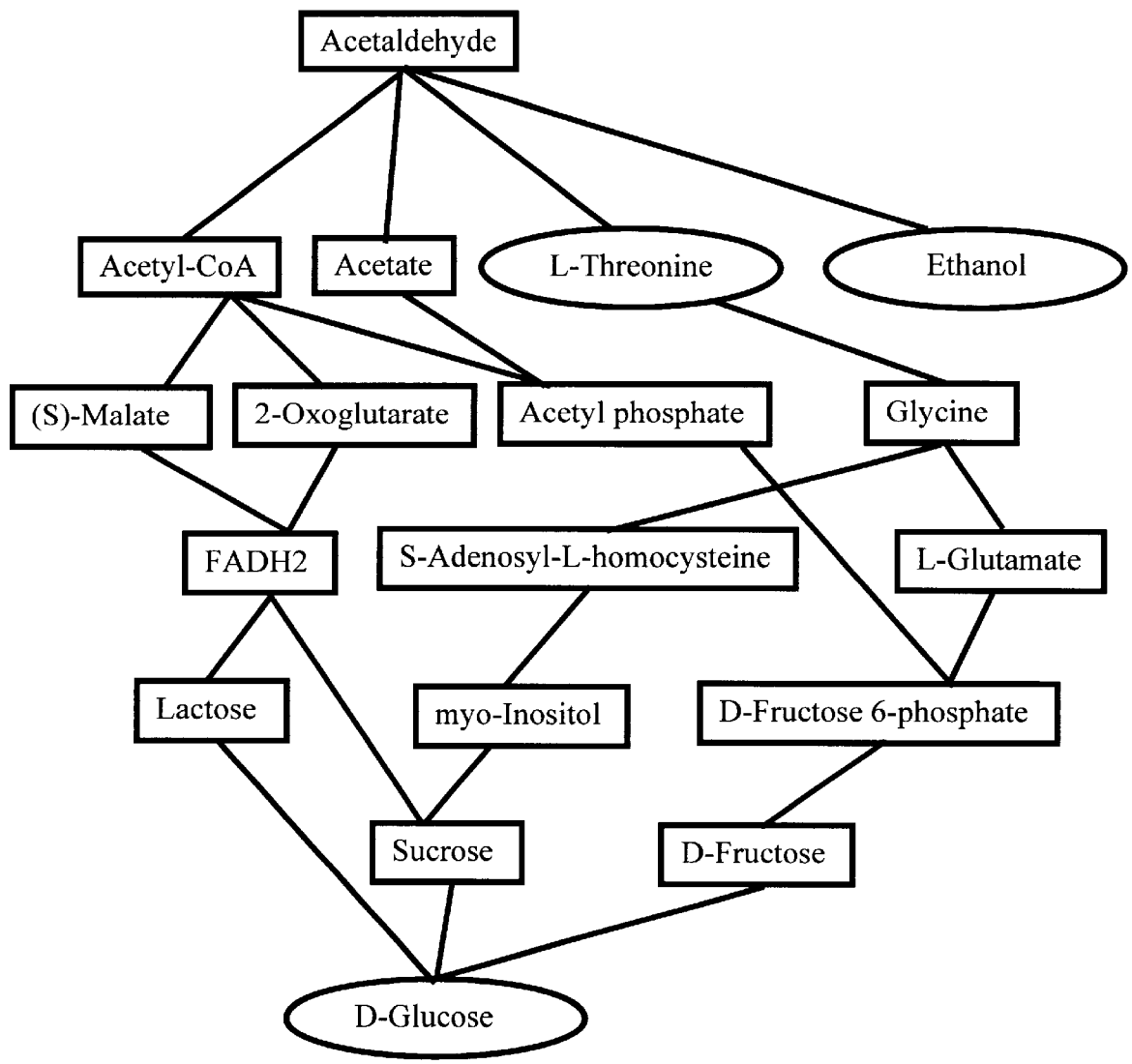
FIG. 8 is a Steiner subgraph comprising a set of overlayed Steiner Trees.

When run, pathmap.m produces multiple Steiner subgraphs that have an equivalent number of edges. The Steiner subgraphs can be visualized with a software utility called "aisee" (available at http://www.absint.com/aisee/). The resulting Steiner Trees can be overlayed to produce a single network, which is shown in FIG. 8. By overlaying the individual Steiner Trees, all potential associations can be examined at one time. As seen in FIG. 8, the context set of this example, D-Glucose, L-Threonine, and Ethanol are vertices in the overlayed Steiner subgraph.

I claim:

1. A method for analyzing biological elements, comprising:
    a) providing a first set of biological elements;
    b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
    c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said first set of biological elements represent genes with increased RNA transcription and said second set of biological elements are genes.

2. The method as in claim 1, wherein said genes with increased RNA transcription are selected based on a single RNA transcription profiling.

3. A method for analyzing biological elements, comprising:
    a) providing a first set of biological elements;
    b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
    c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said first set and said second set comprise elements that are not all of a single type.

4. A method for analyzing biological elements, comprising:
    a) providing a first set of biological elements;
    b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
    c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said algorithm is selected from the group consisting of the shortest path heuristic, the minimum spanning tree heuristic, the distance network heuristic, and the simulated annealing heuristic.

5. A method for analyzing biological elements, comprising:
    a) providing a first set of biological elements;
    b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
    c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said algorithm comprises a minimum spanning tree heuristic.

6. A method for analyzing biological elements, comprising:
    a) providing a first set of biological elements;
    b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements;
    c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements; and, d) repeating steps a) through c), wherein said algorithm creates one or more additional Steiner subgraphs with more edges than said first Steiner subgraph.

7. A method for analyzing biological elements, comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said edges in said graph are differentially weighted.

8. The method as in claim 7, wherein said edges are differentially weighted according to known biorelationships.

9. The method of claim 7, wherein said algorithm creates a Steiner subgraph with the lowest possible total edge weight said algorithm can determine, and further comprising
   d) repeating steps a) through c), wherein said algorithm creates one or more additional Steiner subgraphs with having edges of greater total edge weight than said first Steiner subgraph.

10. A method for analyzing genes, comprising:
    a) providing a first set of genes;
    b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
    c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said first set of genes represent genes with increased RNA transcription.

11. The method as in claim 10, wherein said genes with increased RNA transcription are selected based on a single RNA transcription profiling.

12. A method for analyzing genes, comprising:
    a) providing a first set of genes;
    b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
    c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said algorithm is selected from the group consisting of the shortest path heuristic, the minimum spanning tree heuristic, the distance network heuristic, and the simulated annealing heuristic.

13. A method for analyzing genes, comprising:
    a) providing a first set of genes;
    b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
    c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said algorithm comprises a minimum spanning tree heuristic.

14. A method for analyzing genes, comprising:
    a) providing a first set of genes;
    b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes
    c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes; and,
    d) repeating steps a) through c), wherein said algorithm creates one or more additional Steiner subgraphs with more edges than said first Steiner subgraph.

15. A method for analyzing genes, comprising:
    a) providing a first set of genes;
    b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
    c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said edges in said graph are differentially weighted.

16. The method as in claim 15, wherein said edges are differentially weighted according to known biorelationships.

17. The method of claim 15, wherein said algorithm creates a Steiner subgraph with the lowest possible total edge weight said algorithm can determine, and further comprising
   d) repeating steps a) through c), wherein said algorithm creates one or more additional Steiner subgraphs having edges of greater total edge weight than said first Steiner subgraph.

18. A program storage device readable by a machine, tangibly embodying a program of instructions executable by a machine to perform method steps to analyze biological elements, said method steps comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said first set of biological elements represent genes with increased RNA transcription and said second set of biological elements are genes.

19. The device as in claim 18, wherein said genes with increased RNA transcription are selected based on a single RNA transcription profiling.

20. A program storage device readable by a machine, tangibly embodying a program of instructions executable by a machine to perform method steps to analyze biological elements, said method steps comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said first set and said second set comprise elements that are not all of a single type.

21. A program storage device readable by a machine, tangibly embodying a program of instructions executable by a machine to perform method steps to analyze biological elements, said method steps comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said algorithm is selected from the group consisting of the shortest path heuristic, the minimum spanning tree heuristic, the distance network heuristic, and the simulated annealing heuristic.

22. A. program storage device readable by a machine, tangibly embodying a program of instructions executable by a machine to perform method steps to analyze biological elements, said method steps comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said algorithm comprises a minimum spanning tree heuristic.

23. A program storage device readable by a machine, tangibly embodying a program of instructions executable by a machine to perform method steps to analyze biological elements, said method steps comprising:
   a) providing a first set of biological elements;
   b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements;
   c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements; and,
   d) repeating steps a) through c), wherein said algorithm creates one or more additional Steiner subgraphs with more edges than said first Steiner subgraph.

24. A program storage device readable by a machine, tangibly embodying a program of instructions executable by a machine to perform method steps to analyze biological elements, said method steps comprising:

a) providing a first set of biological elements;
b) providing a graph representing relationships among a second set of biological elements, wherein said biological elements of said second set of biological elements are represented as vertices of said graph and biorelationships between said biological elements of said second set of biological elements are represented as edges of said graph, and wherein said second set of biological elements comprises said first set of biological elements; and,
c) applying an algorithm capable of generating a Steiner Tree to said first set of biological elements and said graph to create a Steiner subgraph, wherein said Steiner subgraph comprises vertices from said graph corresponding to said first set of biological elements and further comprises edges and vertices from said graph connecting said vertices from said graph corresponding to said first set of biological elements, wherein said edges in said graph are differentially weighted.

25. The device as in claim 24, wherein said edges are differentially weighted according to known biorelationships.

26. The device of claim 24, wherein said algorithm creates a Steiner subgraph with the lowest possible total edge weight said algorithm can determine, and further comprising d) repeating steps a) through c), wherein said algorithm creates one or more additional Steiner subgraghs with having edges of greater total edge weight than said first Steiner subgragh.

27. A program storage device readable by a machine, tangibly embodying a program of instructions executable by a machine to perform method steps to analyze genes, said method steps comprising:

a) providing a first set of genes;
b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said first set of genes represent genes with increased RNA transcription.

28. The device as in claim 27, wherein said genes with increased RNA transcription are selected based on a single RNA transcription profiling.

29. A program storage device readable by a machine, tangibly embodying a program of instructions executable by a machine to perform method steps to analyze genes, said method steps comprising:

a) providing a first set of genes;
b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said algorithm is selected from the group consisting of the shortest path heuristic, the minimum spanning tree heuristic, the distance network heuristic, and the simulated annealing heuristic.

30. A program storage device readable by a machine, tangibly embodying a program of instructions executable by a machine to perform method steps to analyze genes, said method steps comprising:

a) providing a first set of genes;
b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and,
c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said algorithm comprises a minimum spanning tree heuristic.

31. A program storage device readable by a machine, tangibly embodying a program of instructions executable by a machine to perform method steps to analyze genes, said method steps comprising:

a) providing a first set of genes;
b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes;
c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes; and,
d) repeating steps a) through c), wherein said algorithm creates one or more additional Steiner subgraphs with more edges than said first Steiner subgraph.

32. A program storage device readable by a machine, tangibly embodying a program of instructions executable by a machine to perform method steps to analyze genes, said method steps comprising:

a) providing a first set of genes;
b) providing a graph representing relationships among a second set of genes, wherein said genes of said second set of genes are represented as vertices of said graph and biorelationships between said genes of said second set of genes are represented as edges of said graph, and wherein said second set of genes comprises said first set of genes; and, c) applying an algorithm capable of generating a Steiner Tree to said first set of genes and said graph to create a Steiner subgraph, wherein said Steiner subgraph comprises vertices from said graph corresponding to said first set of genes and further comprises edges and vertices from said graph connecting said vertices from said graph corresponding to said first set of genes, wherein said edges in said graph are differentially weighted.

33. The device as in claim 32, wherein said edges are differentially weighted according to known biorelationships.

34. The device of claim 32, wherein said algorithm creates a Steiner subgraph with the lowest possible total edge weight said algorithm can determine, and further comprising d) repeating steps a) through c), wherein said algorithm creates one or more additional Steiner subgraphs with having edges of greater total edge weight than said first Steiner subgraph.

* * * * *